United States Patent [19]
Domanik et al.

[11] Patent Number: 5,559,339
[45] Date of Patent: Sep. 24, 1996

[54] METHOD AND APPARATUS FOR VERIFYING DISPENSE OF A FLUID FROM A DISPENSE NOZZLE

[75] Inventors: Richard A. Domanik, Libertyville, Ill.; Gordon Sohl, Richardson, Tex.; John Kotlarik, Vernon Hills; Noman Abunimeh, Grayslake, both of Ill.

[73] Assignee: Abbott Laboratories, Abbott Park, Ill.

[21] Appl. No.: 332,307

[22] Filed: Oct. 31, 1994

[51] Int. Cl.⁶ .................................................. G01N 15/06
[52] U.S. Cl. ...................... 250/573; 250/222.1; 250/577; 356/379; 340/619; 73/861.41; 422/82
[58] Field of Search ..................... 250/222.1, 573, 250/576, 577; 340/606, 619; 73/293, 861, 861.41; 422/81, 82; 436/53, 180; 356/440, 335, 379

[56] References Cited

U.S. PATENT DOCUMENTS

| | | | |
|---|---|---|---|
| 2,880,764 | 4/1959 | Pelavin | 141/130 |
| 3,143,393 | 8/1964 | de Seguin des Hons | 23/253 |
| 3,600,953 | 8/1971 | Isreeli et al. | 73/423 A |
| 3,759,667 | 9/1973 | Bannister et al. | 23/259 |
| 3,869,252 | 3/1975 | Haug | 23/259 |
| 3,874,850 | 4/1975 | Sorensen et al. | 23/230 B |
| 3,929,413 | 12/1975 | Young et al. | 23/259 |
| 4,253,846 | 3/1981 | Smythe et al. | 23/230 |
| 4,312,341 | 1/1982 | Zissomopoulos et al. | 128/214 E |
| 4,344,429 | 8/1982 | Gupton et al. | 128/214 R |
| 4,420,566 | 12/1983 | Jessop et al. | 436/46 |
| 4,517,302 | 5/1985 | Saros | 436/180 |
| 4,526,754 | 7/1985 | Burns et al. | 422/82 |
| 4,640,821 | 2/1987 | Mody et al. | 422/81 |
| 4,643,580 | 2/1987 | Gross et al. | 356/440 |
| 4,680,270 | 7/1987 | Mitsumaki et al. | 436/52 |
| 4,691,580 | 9/1987 | Fosslien | 73/864.84 |
| 4,703,314 | 10/1987 | Spani | 340/619 |
| 4,752,690 | 6/1988 | James | 250/349 |
| 4,774,055 | 9/1988 | Wakatake et al. | 422/64 |
| 4,853,336 | 8/1989 | Saros et al. | 436/53 |
| 4,861,553 | 8/1989 | Mawhirt et al. | 422/65 |
| 4,896,545 | 1/1990 | Averette | 73/863.01 |
| 5,067,092 | 11/1991 | Hamann | 364/496 |
| 5,094,961 | 3/1992 | del Valle et al. | 436/180 |
| 5,352,887 | 10/1994 | Morgan et al. | 250/222.1 |
| 5,434,430 | 7/1995 | Stewart | 250/573 |

FOREIGN PATENT DOCUMENTS

| | | | |
|---|---|---|---|
| 0479394 | 8/1987 | European Pat. Off. | G01N 33/52 |
| 0473241 | 8/1987 | European Pat. Off. | G01N 33/52 |
| 0570238 | 5/1993 | European Pat. Off. | G01N 35/06 |
| 3732516 | 9/1987 | Germany | G01N 297/749 |
| 4211003 | 10/1992 | Germany | G01F 13/00 |
| 58-011859 | 1/1983 | Japan | G01N 35/06 |
| 59-019858 | 2/1984 | Japan | G01N 35/06 |
| 61-231461 | 10/1986 | Japan | G01N 35/06 |

*Primary Examiner*—Stephone Allen
*Attorney, Agent, or Firm*—Mark C. Bach

[57] ABSTRACT

Embodiments disclosed herein provide apparatuses and methods for verifying dispense of a fluid from a dispense nozzle. According to one method, a path of electromagnetic radiation from a source to a receiver is obstructed with the fluid dispensed from the dispense nozzle. The intensity of the electromagnetic radiation received by the receiver is measured. The measured intensity is compared with a predetermined intensity to verify the dispense of fluid from the dispense nozzle. One apparatus for verifying dispense of a fluid comprises a source of electromagnetic radiation, and a receiver of the electromagnetic radiation from the source of the electromagnetic radiation operatively associated with the source of the electromagnetic radiation such that the electromagnetic radiation from the source is received by the receiver. A path followed by the electromagnetic radiation from the source to the receiver is offset from the fluid exiting end of the dispense nozzle by a predetermined distance such that dispense of fluid and a major drop of fluid depending from the fluid exiting end of the dispense nozzle obstruct the path and such that a minor drop of fluid does not obstruct the path.

16 Claims, 2 Drawing Sheets

METHOD AND APPARATUS FOR VERIFYING DISPENSE OF A FLUID FROM A DISPENSE NOZZLE

BACKGROUND OF THE INVENTION

Embodiments of the present invention generally relate to an apparatus and a method for verifying dispense of a fluid. More specifically, the embodiments relate to an apparatus and a method for verifying fluid dispense in an automated instrument.

Automated instruments are available to perform a number of tasks. One such automated instrument is an analytical instrument. An analytical instrument can perform tests, such as medical diagnostic tests, on a sample. For example, such tests may identify the AIDS virus in a blood sample or other item of interest in a biological sample.

To perform such tests, an analytical instrument may mix the biological sample with a substance, such as a reagent and the like. In some embodiments, these reagents may be fluids. The fluids may be supplied to the biological sample within the medical instrument by a fluid system. The fluid system may include a source of fluid, a pump, a dispense nozzle and a conduit fluidly connecting those elements. The source of fluid may be a container and the like. The pump operates to move fluid from the container toward the dispense nozzle through the conduit. The sample, which may be held in a suitable container, is positioned adjacent the dispense nozzle. When the pump is operated, fluid from the container leaves the nozzle and enters the sample container. Movement of the fluid into the container, if desired, can cause the fluid and the sample to mix.

Illustrating further by example, a given instrument may perform a blood analysis. The instrument adds a predetermined volume of a fluid to a predetermined volume of a blood sample. The fluid reacts with the blood sample. Because of the reaction between the sample and the fluid, an electromagnetic signal or light is sent from the mixture of sample and fluid. A detector in the instrument sees or reads the light sent from the mixture. Appropriate elements of the instrument, such as a computer and the like, interpret the information obtained by the detector and provide an operator with information about the blood sample.

In order for this instrument to perform as intended and to give accurate results, it is desirable that a specific, predetermined amount or volume of fluid be mixed with the sample. If too much or too little fluid is added to the sample, the light sent from the mixture may be different from the proper light sent from the mixture when the predetermined volume of fluid is added. The different light sent from the mixture is interpreted by the computer in the same way as the proper light. Therefore, the computer may give inaccurate information to the operator of the instrument.

The possibility of inaccurate information being given by an instrument is a concern. For example, the test performed may be to see if a unit of blood were infected with the AIDS virus. Assuming that the blood is infected with the AIDS virus, adding too little or too much fluid to the blood sample may result in the instrument telling the operator that the unit of blood is not infected with the AIDS virus.

Many things can cause the wrong amount of fluid to be added to the sample. For instance, the conduit may contain a bubble. The conduit itself may be bent or damaged. The pump may not function properly. A drop of fluid may form on an end of the dispense nozzle. These causes may not be detected by simply monitoring the length of time of pump operation or of fluid leaving the dispense nozzle. Accordingly, it can be appreciated that it is desirable to have an element in the instrument for verifying that the proper, predetermined amount of fluid has left the dispense nozzle during operation of the analytical instrument.

SUMMARY OF THE INVENTION

Embodiments disclosed herein provide apparatuses and methods for verifying dispense of a fluid from a dispense nozzle. According to one method, a path of electromagnetic radiation from a source to a receiver is obstructed with the fluid dispensed from the dispense nozzle. The intensity of the electromagnetic radiation received by the receiver is measured. The measured intensity is compared with a predetermined intensity to verify the dispense of fluid from the dispense nozzle.

One apparatus for verifying dispense of a fluid comprises a source of electromagnetic radiation, and a receiver of the electromagnetic radiation from the source of the electromagnetic radiation operatively associated with the source of the electromagnetic radiation such that the electromagnetic radiation from the source is received by the receiver. A path followed by the electromagnetic radiation from the source to the receiver is offset from the fluid exiting end of the dispense nozzle by a predetermined distance such that dispense of fluid and a major drop of fluid depending from the fluid exiting end of the dispense nozzle obstruct the path and such that a minor drop of fluid does not obstruct the path.

In another method, a source of electromagnetic radiation and a receiver of the electromagnetic radiation from the source of electromagnetic radiation are provided operatively associated with the dispense nozzle. The source is energized such that the source produces electromagnetic radiation. The receiver is illuminated with the electromagnetic radiation. A first signal is generated with the receiver. A threshold is set based on the first signal. Fluid is dispensed from the dispense nozzle. The fluid dispensed from the dispense nozzle obstructs the electromagnetic signal between the source and the receiver. The receiver generates a second signal. The threshold and the second signal are compared to indicate start of a dispense of fluid from the dispense nozzle. The receiver generates a third signal which is compared with the threshold to indicate finish of a dispense of fluid from the dispense nozzle. A first time period between generation of the second signal and generation of the third signal is determined. A second time period representing an expected temporal duration between start and finish of the dispense of fluid from the dispense nozzle is also determined. The first time period and the second time period are compared to verify the dispense of fluid from the dispense nozzle.

According to another method, a source of electromagnetic radiation and a receiver of the electromagnetic radiation from the source of electromagnetic radiation are provided operatively associated with the dispense nozzle for detecting a major drop of fluid depending from the dispense nozzle and for ignoring a minor drop of fluid depending from the dispense nozzle. A threshold relevant to electromagnetic radiation received by the receiver is set. The threshold is sufficient for detection of the major drop and for ignorance of the minor drop. The electromagnetic radiation moving between the source and the receiver is obstructed with the fluid being dispensed from the dispense nozzle to generate a signal with the receiver. The signal is compared with the threshold to verify a dispense of the fluid from the dispense nozzle.

DETAILED DESCRIPTION OF PREFERRED EMBODIMENTS

Figure 1:
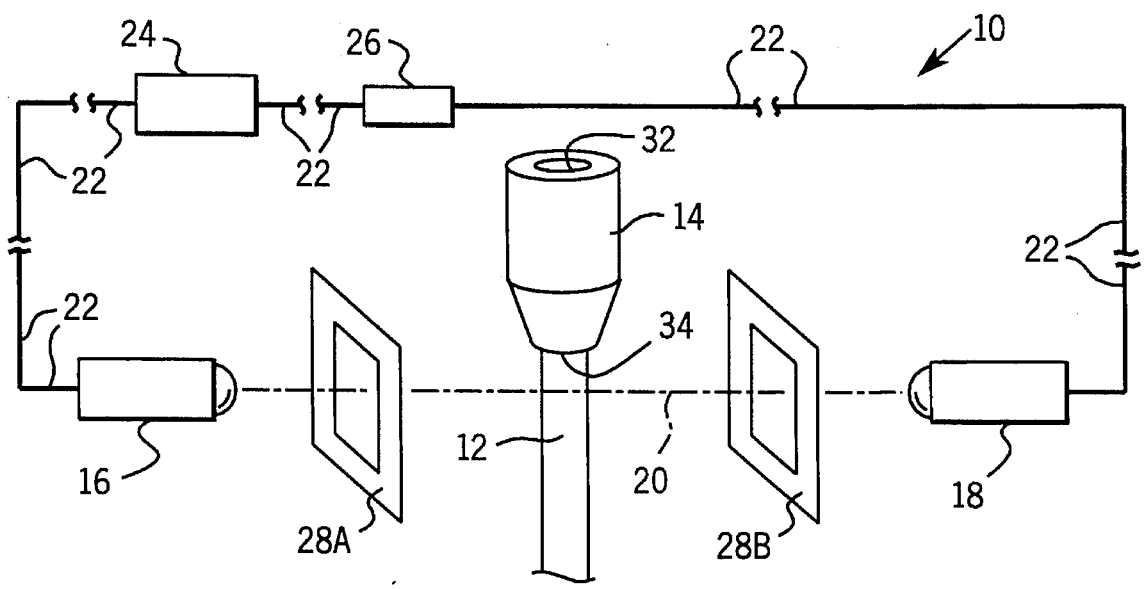
FIG. 1 generically illustrates an apparatus for verifying dispense of a fluid.

FIG. 1 illustrates one embodiment 10 of an apparatus and a method for verifying dispense of a fluid 12 from a dispense nozzle 14. Dispense verification, as will become clear herein, refers to obtaining information about the status of a fluid dispense, detecting a major hanging drop of fluid, checking temporal duration of a dispense, etc. In the embodiments discussed herein, dispense verification utilizes an electromagnetic radiation intensity measurement, possibly coupled with a temporal measurement.

For the sake of clarity of understanding, the embodiments of the apparatus and method will be discussed with respect to their employment with an analytical instrument. For instance, the embodiments may be used with the instruments and methods disclosed in U.S. Pat. Nos. 5,006,309, 5,089,424, 5,120,199, 5,185,264, 5,198,368 and 5,244,630. Those patents are assigned to the assignee of the present case and the disclosures thereof are specifically incorporated herein, in their entirety, by this reference. However, it is to be recognized that each of the embodiments may have other employments without departing from the scope of the claims.

Furthermore, structures and method steps of one embodiment may be combined, in any suitable fashion, with structures and method steps of another embodiment to arrive at still further embodiments. For instance, multiple embodiments may be integrated along a processing path in a single instrument. While the fluid 12 may be understood to be a reagent, other fluids are also possible. It may be desirable to locate an apparatus at every fluid addition location apt to cause a false result or inaccurate information being given to an instrument operator. Illustrating by example, in an analytical instrument, dispense verification apparatus may be located where particles, conjugates and/or probes are added to sample and where washes occur.

Returning to FIG. 1, the embodiment 10 comprises a source 16 of electromagnetic radiation and a receiver 18 operatively associated with the dispense nozzle 14. The source 16 and the receiver 18 are disposed with respect to the dispense nozzle 14 such that flow of fluid 12 from the nozzle 14 passes through a path 20 of electromagnetic radiation from the source 16 to the receiver 18. It is to be noted that the path 20 passes through an ambient fluid, such as air. No lenses or filters are required. As will be discussed in further detail later, passage of fluid 12 through the path 20 allows for dispense verification.

The source 16 and the receiver 18 are predetermined such that the receiver 18 generates a signal responsive to electromagnetic radiation sent from the source 16. In an exemplary embodiment, the source 16 may be a light emitting diode and the like. In a specific embodiment, the source 16 is capable of emitting electromagnetic radiation of about 900 nm (infrared). The receiver 18, in an exemplary embodiment, may be a phototransistor and the like. If the source 16 were a diode emitting electromagnetic radiation at about 900 nm, then the receiver 18 would be chosen such that a peak sensitivity of the receiver 18 would be in substantially the same range of the electromagnetic spectrum. If the infrared portion of the electromagnetic spectrum were used in the embodiment 10, then the amount of energy present in the photons travelling from the source 16 to the receiver 18 would be reduced. In a specific embodiment, the source 16 is an SEP8706-002 and the receiver 18 is an SDP8406-003, both being available from Honeywell, MICRO SWITCH, Optoelectronics Division of Richardson, Tex.

In the illustrated embodiments, the source 16 and the receiver 18 are electrically connected by a wire 22 to other supporting electronics, such as a controller 24 through a preamplifier 26, for instance. The source 16 is supplied with power at a substantially constant level. Thus, if multiple embodiments 10 were included in a specific instrument, then all embodiments may be compared against a common threshold, discussed later.

In the illustrated embodiment, the preamplifier 26 presents a relatively high input impedance to match the impedance of the receiver 18. The preamplifier 26 also presents a relatively low impedance to match the impedance of the controller 24. The relatively low impedance facilitates signal transmission along conduit 22 toward controller 24. In an exemplary embodiment, the controller 24 comprises a processor, such as a Motorola (Schaumburg, Ill.) 68HC11F1 and the like, and a digital-to-analog converter, such as a 7228A, available from Analog Devices, Inc. of Norwood, Mass., and the like. If multiple apparatuses 10 were provided, then the controller 24 can include a multiplexer, such as one handling about six outputs and about 12 inputs. The outputs would drive, up to about 5 mA, two source 16/receiver 18 pairs connected electrically in series. Such a circuit can incorporate current feedback to provide a substantially linear response. In one embodiment, the multiplexer is predetermined to have a frequency response sufficient for about 98% setting in about 130 microseconds. In this manners switching of source 16 drives and multiplexer input signals would be appropriately chosen such that the 12 inputs could be read, approximately, every 1.6 msec.

In a specific embodiment, the preamplifier 26 drives two source 16/receiver 18 pairs selectively with two predetermined electrical signals. For the sake of clarity, a first pair of source 16/receiver 18 is designated the "A" pair, while the other pair is designated the "B" pair. The A and B pairs are electrically connected in series with the preamplifier 26. The preamplifier 26 drives the A and B pairs at a predetermined electrical signal appropriate for the A pair. The output of the receiver 18 in the A pair is monitored. Then, the preamplifier 26 drives the A and B pairs at a predetermined electrical signal for the B pair. The output of the B receiver 18 is monitored. If a plurality of A and B pairs were provided, then all of the pairs would be driven with the A electrical signal, the output of the A receivers 18 would be monitored sequentially, then all of the pairs would be driven with the B electrical signal and the output of all of the B receivers 18 would be monitored sequentially.

In this manner, the electrical signal driving all of the sources 16 is not constant. The A electrical signal is applied to the source 16 and the output of the associated receiver 18 is monitored after it settles. The B electrical signal is applied and the output of the B receiver 18 is monitored. This process can repeat at a rate of about 1250 times per second. Thus, each receiver 18 output is monitored about 625 times each second. Accordingly, during a dispense cycle, the receiver 18 output can be monitored about 80 times while the output is below the threshold. This can result in an error tolerance of about one percent.

In still other embodiments, the controller 24 may be provided with access, such as an RS232 port, to a computer for monitoring, controlling and trouble shooting the apparatus 10. The computer or other electronic element operatively associated with the access may provide a feedback signal to an operator indicative of the status of dispense of fluid 12 from the dispense nozzle 14.

In the embodiment 10 shown in FIG. 1, the source 16 and the receiver 18 are offset from the path of fluid 12 flow from the dispense nozzle 14 by screens 28A and 28B, respectively. The screens 28A and 28B are constructed and located to reduce the chance that fluid 12 flowing from the dispense nozzle 14 might reach the source 16 or the receiver 18. If fluid 12 were to reach either the source 16 or the receiver 18, then the embodiment 10 may not operate as intended. The screens 28A and 28B may also be used if it were desired to avoid cleaning the source 16 and/or the receiver 18. In this embodiment, the screens 28A and 28B could be cleaned instead of the source 16 and receiver 18.

Figure 2:
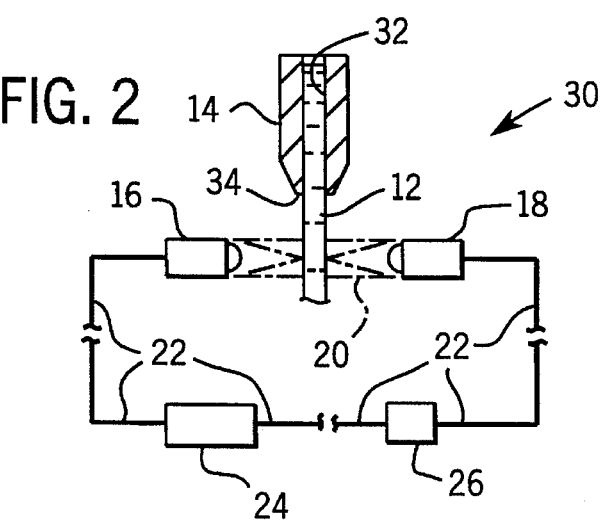
FIG. 2 illustrates another embodiment of the apparatus shown in FIG. 1.

However, fluid 12 reaching the source 16 and/or the receiver 18 may not always be a concern. This may depend upon the characteristics of the fluid 12. If fluid 12 reaching the source 16 or the receiver 18 were not a concern, then one or both of the screens 28A and 28B may be eliminated. FIG. 2 illustrates an embodiment 30 of an apparatus for verifying dispense of fluid 12 from dispense nozzle 14 which does not comprise screens 28A and 28B. The embodiment 30 is substantially similar to the embodiment 10 of FIG. 1, hence the like reference numerals for similar structures. Both embodiments 10 and 30 function substantially the same.

Figure 3:
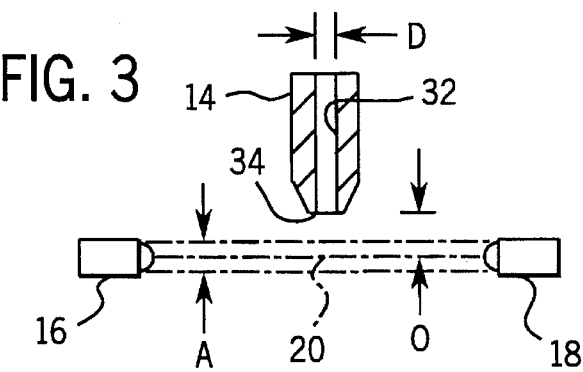
FIG. 3 is a schematic view of an apparatus for verifying dispense of a fluid showing relative positions of elements of the apparatus.

The relative locations of the nozzle 14, the source 16 and the receiver 18 assist in intended operation of the embodiments 10 and 30. These relative locations are illustrated in FIG. 3. The dimensions given in the following paragraphs are for the purposes of illustration only and are not intended to limit the scope of the claims.

In an exemplary embodiment, the dispense nozzle 14 comprises a bore 32 having a diameter D of about 0.030 inches. Therefore, a stream of fluid 12 leaving the dispense nozzle 14 has a diameter of about 0.030 inches.

The source 16, which illuminates relevant portions of the receiver 18 with electromagnetic radiation, and the receiver 18 are mutually exposed through an aperture having a diameter A of about 0.062 inches. The apertures, in one embodiment, may be formed by a suitable technique, such as machining and the like, in a mounting bracket, formed from a suitable material such as aluminum and the like, operatively associated with the source 16 and the receiver 18. The apertures define dimensions of a latitudinal cross section of the path 20 of electromagnetic radiation from the source 16 to the receiver 18. Thus, during dispense of fluid 12 from the nozzle 14, the fluid 12 will encounter or block about half of the latitudinal cross section of the path 20.

A longitudinal axis of the path 20 is offset from a fluid-exiting end 34 of the dispense nozzle 14 by a specific, predetermined distance O, shown in FIG. 3. In an exemplary embodiment, the distance O is about 0.10 inches. The distance O is chosen so that the embodiments 10 and 30 are able to sense a significant volume of fluid 12 depending from the end 34 of the dispense nozzle 14. Put in another way, the distance O is chosen such that the embodiments 10 and 30 detect a major drop of fluid 12 and avoid a minor drop of fluid 12 depending or hanging from the end 34 of the nozzle 14.

A major drop of fluid 12 contains a volume of fluid 12 sufficient to significantly adversely affect dispense of an intended volume of fluid 12 from the nozzle 14, whereas a minor drop of fluid 12 does not have sufficient volume of fluid 12 to significantly adversely affect dispense of an intended volume of fluid 12. Thus, it can be appreciated that, by avoiding detection of minor hanging drops of fluid 12, the likelihood of sensing a dispense incorrectly can be reduced. However, detecting major hanging drops is desirable because a major hanging drop can significantly affect dispense of fluid 12 from the dispense nozzle 14. If the dispense of fluid 12 were significantly affected, then it is possible that the instrument associated with the dispense nozzle 14 could give the instrument operator incorrect information about a sample being tested.

Detection of a major hanging drop is also dependent upon a threshold applied to a signal generated by the receiver 18. The threshold is a predetermined percentage of electromagnetic signal (i.e. electromagnetic intensity) sent from the source 16 and received by the receiver 18. The threshold may be considered to represent a portion of the electromagnetic signal sent from the source 16 and blocked from reaching the receiver 18 by fluid 12 depending or dispensed from the dispense nozzle 14. The value of the threshold is predetermined such that the embodiments 10 and 30 can detect fluid dispense status and a major hanging drop and ignore a minor hanging drop. Determination of the threshold will be discussed in detail later. The embodiments 10 and 30, as well as all supporting electronics, are constructed to provide feedback dependent upon a comparison of electromagnetic intensity received by the receiver 18 with the threshold, thereby indicative of fluid dispense status and/or hanging drops, to the operator.

For example, if the threshold were set at about 90% of the source 16 intensity, then the embodiments 10 and 30 could indicate presence of a hanging drop if the receiver 18 was illuminated by the source 16 at a level of less than about 90% of the level of illumination of the receiver 18 by the source 16 when no fluid 12 is present (i.e. a quiescent state). Thus, the embodiments 10 and 30 would indicate an erroneous dispense if the electromagnetic radiation received by the receiver 18 were to fall by about 10% from its quiescent state.

If the receiver 18 threshold were set to detect an about 10% drop in electromagnetic intensity sent by the source 16, then the embodiments 10 and 30 would detect a drop of fluid 12, having a fluid volume as small as about 10 μl, for example, depending from the end 34 of the nozzle 14. In this manner, the effects of things which cause a dispense of fluid 12 from the nozzle 14 to decrease or trail off relatively slowly at the end of a dispense cycle, rather than the dispense cycle ending abruptly, can be detected.

With the construction of the embodiments 10 and 30 being discussed in detail, a method of operation of the embodiment 10 and 30 will now be described. Both of the embodiments 10 and 30 operate in substantially the same manner. Thus, the following discussion applies equally to both embodiments 10 and 30. It is to be remembered that the method steps disclosed below may be performed in any suitable order. Furthermore, steps of different methods may be combined in any desirable order to arrive at still other methods.

It is assumed that no fluid 12 has left the dispense nozzle 14 so that no fluid 12 has passed through the nozzle 14 to form a hanging drop. The source 16 is energized to produce an electromagnetic signal of predetermined characteristics. The electromagnetic signal travels from the source 16 along the path 20 to the receiver 18. The source 16 generates this electromagnetic signal substantially continuously during operation of the embodiments 10 and 30. If the embodiments 10 and 30 were included in an analytical instrument, then, in one embodiment, the source 16 would generate the electromagnetic signal throughout substantially the entire duration of analytical instrument operation. At this point, the receiver 18 is at the quiescent state. The electromagnetic signal received by the receiver 18 at this time is defined as the quiescent or reference signal.

The substantially continuous operation of the source 16 allows for substantially fail-safe operation of the embodiments. Specifically, as will become clear herein, the electromagnetic signal travels from the source 16 to the receiver 18 substantially continuously so that any deviation, as determined by the controller 24, in transmitted signal intensity, received by the receiver 18 can be used to provide feedback indicative of fluid 12 dispense from the nozzle 14 to the operator.

The intensity of the electromagnetic signal transmitted by the source 16 and received the receiver 18 is used to determine the threshold discussed earlier. If there were multiple embodiments 10 and 30 in a given instrument, then all of the embodiments may be set to the same threshold. In an exemplary embodiment, because the flow of fluid 12 from the nozzle 14 during an intended fluid dispense cycle will pass through about half of the path 20 of electromagnetic radiation from the source 16 to the detector 18, the threshold may be selected to be about 75% of the quiescent state signal.

Illustrating further by example, in one embodiment, the source 16 driving signal is adjusted prior to dispense of fluid 12 from the dispense nozzle 14. The source 16 driving signal is adjusted so that the quiescent signal is at a desired, predetermined level above the threshold. The source 16 driving signal can be adjusted within the range of a maximum and a minimum source 16 driving signal associated with the relevant source 16. If it were not possible to adjust the source 16 driving signal such that the quiescent signal is above the threshold by the desired amount, then an error message may be reported to an operator. Thus, functionality of the associated source 16/receiver 18 pair is verified.

In some embodiments, it may be desirable to detect a major hanging drop. Therefore, in these embodiments, it may be desirable to set the threshold substantially within the range of about 80% to about 90% of the quiescent signal. The exact value of the threshold may depend on a number of factors, such as physical dimensions of the embodiments 10 and 30, characteristics of the fluid 12, etc. The threshold value may be determined by and stored in memory, such as a RAM, ROM, EPROM, SRAM and the like running appropriate routines, present in or associated with the controller 24. The controller 24 may update the threshold as necessary, thereby possibly allowing for obstructions, such as dust, other than fluid 12 in the path 20. These obstructions may accumulate over time, thereby making updating of the threshold desirable.

With the threshold set, fluid 12 dispense cycles can begin. As fluid 12 exits the dispense nozzle 14, the fluid 12 passes through the path 20 and correspondingly reduces the intensity of the electromagnetic signal reaching the receiver 18. The electromagnetic intensity received by the receiver 18 is monitored by the controller 24.

In some embodiments, the controller 24 may contain a timer to monitor duration of the reduction in received electromagnetic intensity. In these embodiments, the controller 24 monitors the time interval during which the electromagnetic intensity received by the receiver 18 is reduced below the predetermined threshold. The end of the dispense cycle is determined by the intensity received by the receiver 18 returning to a value greater than the threshold. The time between the moment the received intensity falls below the threshold and the moment the received intensity rises above the threshold is an actual temporal duration of the dispense cycle. This actual temporal duration is compared to a predetermined, expected temporal duration of the dispense cycle, which may be determined empirically. The expected temporal duration may depend on fluid 12 pump tolerances, conduit length from pump to the end 34 of the dispense nozzle 14, etc. In an exemplary embodiment, an expected temporal duration may be about 124 msec. to about 144 msec. If the two temporal durations were substantially the same, then the controller 24 can cause feedback indicative of a proper dispense to be sent to the operator. If the actual and expected durations were not substantially the same, then the controller 24 can cause feedback indicative of an improper dispense to be sent to the operator.

Figure 4:
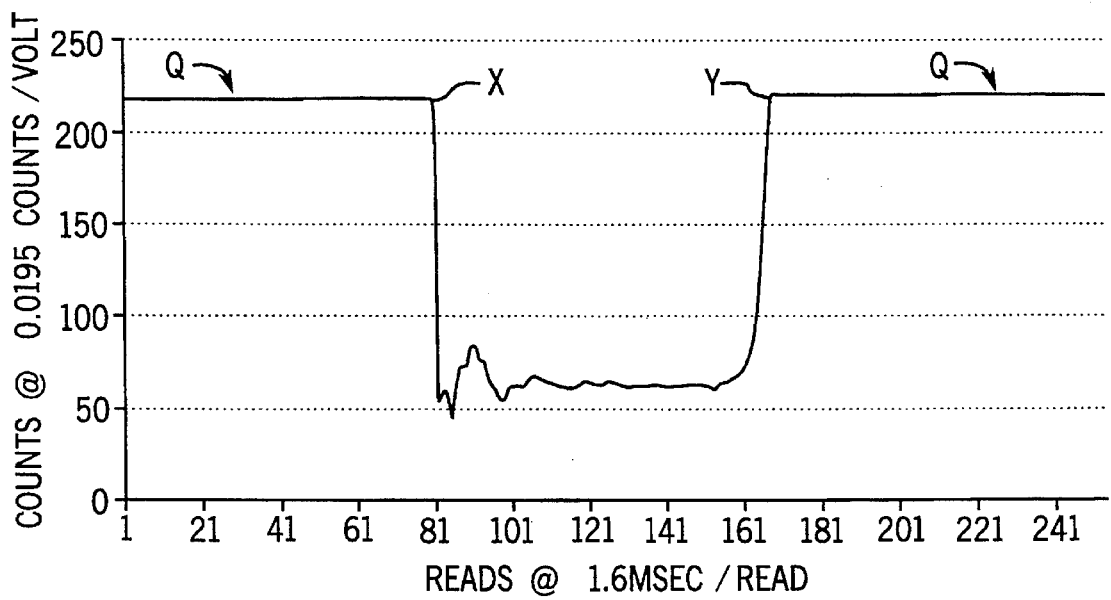
FIG. 4 is a graph of an electronic signal generated by a receiver responsive to a signal sent by a source comprising an apparatus of verifying dispense.

In an exemplary embodiment, an electronic signal generated by the receiver 18 responsive to the electromagnetic signal sent by the source 16 during a proper dispense is shown in FIG. 4. In this example, it is assumed that the threshold is set at about 90% of the quiescent signal Q and the expected temporal duration for a proper dispense is substantially within the range of 124 and 144 msec.

As the graph shows, the dispense cycle begins, labelled "X" in FIG. 4, and fluid 12 flowing from the dispense nozzle 14 blocks a portion of the path 20. The fluid 12 reduces the intensity of the electromagnetic signal received by the receiver 18. The received intensity is reduced sufficiently such that it falls below the predetermined threshold value. This reduction in received intensity lasts for about 138 msec (actual temporal duration). When the dispense cycle ends, indicated by "Y" in FIG. 4, the received intensity increases, rises above the threshold value and approaches the quiescent signal Q. The controller 24 compares the actual and expected temporal durations. Because the two durations are substantially identical, this dispense is a proper dispense. If desired, the controller 24 can cause a relevant feedback signal to be sent to the operator.

Signal transmission from the source 16 to the receiver 18 continues. If desired, it is possible to reset the threshold. This may be desirable if, for reasons other than a hanging drop, such as dust and the like, the received intensity were not to return to the quiescent signal. The embodiments 10 and 30 are ready for verification of another dispense.

Improper dispenses can have a number of causes. One of the causes may be a gas, i.e. air bubble and the like, in the fluid 12 path from a fluid 12 stock container to the end 34 of the dispense nozzle 14. Many things may cause gas to be present in the fluid path. For instance, the fluid 12 system may have been improperly "primed", the fluid 12 stock container may be almost empty, connections in the fluid 12 system may leak, fluid 12 may be restricted, there may be effects due to siphoning, etc.

If a gas were in the fluid line, then the actual temporal duration may be shortened. This can occur without changing substantially the volume of fluid 12 dispensed from the dispense nozzle 14. The gas in the line may be compressed during initial activation of a pump forcing fluid 12 through the line supplying the dispense nozzle 14, thereby possibly causing a delay in beginning the dispense. In addition, at the end of the dispense cycle, the velocity of the fluid 12 leaving the end 34 of the dispense nozzle 14 may be greater than the fluid velocity generated by the pump. The increased fluid 12 velocity can cause the desired volume of fluid 12 to leave the dispense nozzle 14 before the expiration of the expected temporal duration. Also, the increased fluid 12 velocity can cause fluid 12 to splash into unintended places.

Build-up of fluid 12 residue, which may be caused by fluid 12 evaporating from the end 34 of the nozzle 14, may direct fluid 12 from the end 34 of the dispense nozzle 14 in an unintended direction. Misdirection of fluid 12 from the end 34 of the dispense nozzle 14 during a dispense cycle may result in an improper dispense which is also detectable by the embodiment 10. Thus, the embodiment 10 can also verify that fluid 12 was dispensed from the dispense nozzle 14 in an intended path or direction.

Another cause of improper dispenses may be a drop of fluid 12 depending or hanging from the end 34 of the dispense nozzle. The hanging drop may be formed by fluid pressure being relieved through the dispense nozzle 14. This may be caused by a "kink" or other restriction in the fluid line supplying fluid 12 to the dispense nozzle 14. A hanging drop may become a restriction to fluid 12 leaving the nozzle 14 through the end 34. Depending upon the composition of the fluid 12 and the time of duration of the hanging drop, it is possible that the fluid 12 comprising the drop may dry on the dispense nozzle 14. Also, it is possible that fluid 12 hanging from the end 34 of the nozzle 14 in the form of a drop may fall off of the end 34 of the nozzle 14 at an unadvantageous time. The falling drop may cause erroneous information to be given to the operator. Thus, it is recommended that all data associated with tests involving an improper dispense be discarded.

Figure 5:
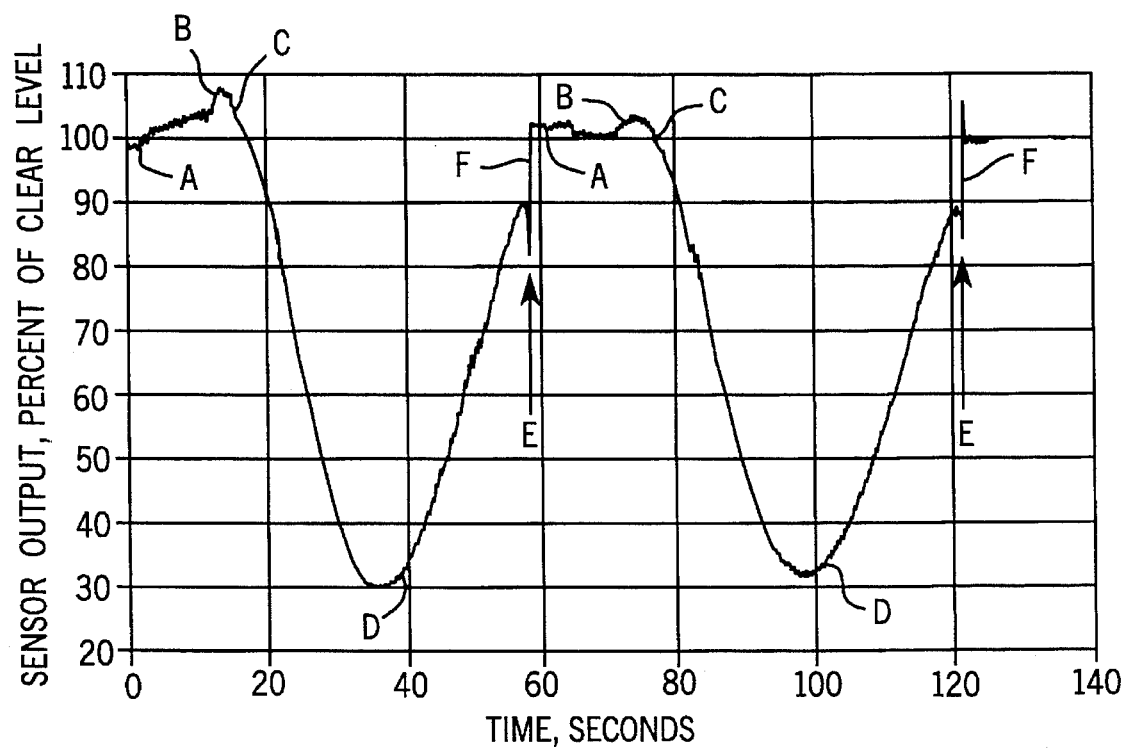
FIG. 5 is a graph similar to FIG. 4 showing an improper dispense.

To further clarify, in an exemplary embodiment, an electronic signal generated by the receiver 18 responsive to the electromagnetic signal sent by the source 16 during an improper dispense is shown in FIG. 5. For the sake of clarity, the threshold and the expected temporal durations are assumed to be the same as described above. During the time period illustrated, it is not intended to dispense any fluid 12 from the nozzle 14. The improper dispense, in this example, is the result of a major hanging drop. The major hanging drop may have been caused by fluid 12 slowing leaking from the end 34 of the dispense nozzle 14. This may be indicative of a defect in the nozzle 14 or in the conduit supplying fluid 12 to the nozzle 14.

The received signal, at point A in FIG. 5, is at about the quiescent signal. As time progresses, more fluid 12 leaks from the end 34 of the nozzle 14. A drop begins to form at the end 34. The drop of fluid 12 directs stray light back into the path 20 of electromagnetic radiation from the source 16 to the receiver 18. The direction of stray light into the path 20 causes the received intensity to increase, as shown at B.

The received intensity increases until a portion of the drop of fluid 12 depending from the end 34 of the nozzle 14 begins to obstruct a portion of the path 20 between the source 16 and the receiver 18. At this point C, the received intensity of electromagnetic intensity begins to decrease. The received intensity decreases until the drop of fluid 12 is sufficient to substantially focus or direct electromagnetic radiation from the source 16 onto the receiver 18. As shown, the received intensity increases due to the redirection effected by the drop of fluid 12 hanging from the end 34 of the dispense nozzle 14.

The size of the hanging drop continues to grow as more and more fluid 12 leaks from the dispense nozzle 14. The size of the drop increases until forces of the system, e.g. gravity, surface tension, adhesion, etc., are insufficient to maintain the drop of fluid 12 on the end 34 of the dispense nozzle 14. At this point, labelled E, the drop falls off of the end 34 of the dispense nozzle 14. Because there is substantially no fluid 12 depending from the end 34 of the nozzle 14, the path 20 is substantially unobstructed. The received intensity increases, labelled F, toward the quiescent signal. Because fluid 12 continues to leak from the end 34 of the nozzle 14, the above-described behavior repeats.

Given the above examples, it is evident how any conditions relevant to a fluid 12 dispense from the dispense nozzle 14 can be monitored by the embodiments 10 and 30 with appropriate modifications to the disclosed structures. For instance, the distance between the end 34 of the dispense nozzle 14 and the longitudinal mid line of the path 20 may be determined to allow detection of minor hanging drops. The threshold may be predetermined to allow detection of air bubbles, clots, inhomogeneities, etc. in the dispensed fluid 12 as it flows from the end 34 of the dispense nozzle 14.

What is claimed is:

1. A method for verifying dispense of a fluid from a dispense nozzle, the method comprising the steps of:

(a) providing a source of electromagnetic radiation and a receiver of the electromagnetic radiation from the source of electromagnetic radiation operatively associated with the dispense nozzle in an analytical instrument;

(b) energizing the source such that the source produces electromagnetic radiation;

(c) illuminating the receiver with the electromagnetic radiation;

(d) generating with the receiver a first signal;

(e) setting a threshold based on the first signal;

(f) dispensing fluid from the dispense nozzle;

(g) obstructing the electromagnetic signal between the source and the receiver with the fluid dispensed from the dispense nozzle;

(h) generating with the receiver a second signal;

(i) comparing the threshold and the second signal to indicate start of a dispense of fluid from the dispense nozzle;

(j) generating with the receiver a third signal;

(k) comparing the third signal and the threshold to indicate finish of a dispense of fluid from the dispense nozzle;

(l) determining a first time period between generation of the second signal and generation of the third signal;

(m) determining a second time period representing an expected temporal duration between start and finish of the dispense of fluid from the dispense nozzle;

(n) comparing the first time period and the second time period to verify the dispense of fluid from the dispense nozzle; and (o) updating the threshold after expiration of the second time period.

2. A method as defined in claim 1 further comprising the step of:

(p) locating the source and the receiver with respect to the dispense nozzle such that a major volume of fluid, sufficient to significantly adversely effect dispense of an intended volume of fluid, hanging from the dispense nozzle obstructs the electromagnetic signal between the source and the receiver.

3. A method as defined in claim 1 further comprising the step of:

(p) setting the threshold such that a major volume of fluid, sufficient to significantly adversely effect dispense of an intended volume of fluid, hanging from the dispense nozzle is detected.

4. A method as defined in claim 1 further comprising the steps of:

(p) generating a feedback signal indicative of a result of step (n); and (q) providing the feedback signal to an operator.

5. A method as defined in claim 1 further comprising the steps of:

(p) defining a path of electromagnetic radiation having a longitudinal axis between the source and the receiver; and (q) offsetting the longitudinal axis of the path of electromagnetic radiation between the source and the receiver from a fluid exiting end of the dispense nozzle by a distance of about 0.1 inches.

6. A method as defined in claim 1 further comprising the step of:

(p) locating the source and the receiver with respect to the dispense nozzle such that a minor volume of fluid, not sufficient to significantly adversely affect dispense of an intended volume of fluid, hanging from the dispense nozzle does not significantly obstruct the electromagnetic signal between the source and the receiver.

7. A method as defined in claim 1 further comprising the step of:

(p) setting the threshold such that a minor volume of fluid, not sufficient to significantly adversely affect dispense of an intended volume of fluid, hanging from the dispense nozzle is not detected.

8. A method as defined in claim 1 further comprising the step of:

(p) inhibiting fluid dispensed from the dispense nozzle from reaching at least one of the source and the receiver.

9. A method for verifying a dispense of a fluid from a dispense nozzle, the method comprising the steps of:

(a) providing a source of electromagnetic radiation and a receiver of the electromagnetic radiation from the source of electromagnetic radiation operatively associated with the dispense nozzle in an analytical instrument for detecting a major volume of fluid, sufficient to significantly adversely effect dispense of an intended volume of fluid, hanging from the dispense nozzle and for ignoring a minor volume of fluid, not sufficient to significantly adversely affect dispense of an intended volume of fluid, from the dispense nozzle;

(b) setting a threshold relevant to electromagnetic radiation received by the receiver, the threshold being sufficient for detection of the major volume and for ignorance of the minor volume;

(c) obstructing the electromagnetic radiation transmitted between the source and the receiver with the fluid being dispensed from the dispense nozzle to generate a signal with the receiver; and (d) comparing the signal with the threshold to verify a dispense of the fluid from the dispense nozzle.

10. A method as defined in claim 9 further comprising the steps of:

(e) defining a path of electromagnetic radiation having a longitudinal axis between the source and the receiver; and (f) offsetting the longitudinal axis of the path of electromagnetic radiation between the source and the receiver from a fluid exiting end of the dispense nozzle by a distance of about 0.1 inches.

11. A method as defined in claim 9 further comprising the step of:

(e) inhibiting fluid dispensed from the dispense nozzle from reaching at least one of the source and the receiver.

12. A method as defined in claim 9 further comprising the step of:

(e) updating the threshold.

13. An apparatus for verifying dispense of a fluid from a fluid exiting end of a dispense nozzle, the apparatus comprising:

(a) a source of electromagnetic radiation;

(b) a receiver of the electromagnetic radiation from the source of the electromagnetic radiation operatively associated with the source of the electromagnetic radiation such that the electromagnetic radiation from the source is received by the receiver; and (c) a path followed by the electromagnetic radiation from the source to the receiver offset from the fluid exiting end of the dispense nozzle by a predetermined distance such that dispense of fluid and a major volume of fluid, sufficient to significantly adversely effect dispense of an intended volume of fluid, hanging from the fluid exiting end of the dispense nozzle obstruct the path and such that a minor volume of fluid, not sufficient to significantly adversely affect dispense of an intended volume of fluid, does not obstruct the path.

14. An apparatus as defined in claim 13 wherein the path is offset from the fluid exiting end of the dispense nozzle by about 0.1 inches.

15. An apparatus as defined in claim 13 further comprising (d) a controller operatively associated with the receiver for comparing a signal generated by the receiver responsive to the electromagnetic radiation to a predetermined signal.

16. An apparatus as defined in claim 15 further comprising (e) a timer for measuring a time period during which the signal generated by the receiver falls below the predetermined signal.

* * * * *